United States Patent [19]

Delpy

[11] Patent Number: 5,251,632
[45] Date of Patent: Oct. 12, 1993

[54] TISSUE OXYGEN MEASURING SYSTEM

[75] Inventor: David T. Delpy, London, United Kingdom

[73] Assignee: Hamamatsu Photonics K.K., Shizuoka, Japan

[21] Appl. No.: 727,168

[22] Filed: Jul. 9, 1991

[30] Foreign Application Priority Data

Mar. 7, 1991 [EP] European Pat. Off. ............ 91301920

[51] Int. Cl.$^5$ .............................................. A61B 5/00
[52] U.S. Cl. ................................. 128/633; 128/204.23
[58] Field of Search ................... 128/633, 666, 204.23, 128/204.22, 205.23, 691; 356/41

[56] References Cited

U.S. PATENT DOCUMENTS

| 4,223,680 | 9/1980 | Jobsis. | |
|---|---|---|---|
| 4,665,911 | 5/1987 | Williams | 128/204.23 |
| 4,765,340 | 8/1988 | Sukai et al. . | |
| 4,824,242 | 4/1989 | Frick et al. . | |
| 4,889,116 | 12/1989 | Taube | 128/633 |
| 4,901,238 | 2/1990 | Suzuki et al. . | |
| 4,924,874 | 5/1990 | Murose | 128/682 |
| 5,103,814 | 4/1992 | Maher | 128/204.18 |

FOREIGN PATENT DOCUMENTS 0267978  5/1988  European Pat. Off. .
63-275324 11/1988  Japan .

OTHER PUBLICATIONS

"Cotside measurement of cerebral blood flow in ill newborn infants by near infrared spectroscopy", The Lancet; Oct. 1, 1988, A. D. Edwards et al., pp. 770–771.
"Quantitation of cerebral blood volume in human infants by near-infrared spectroscopy", J. Appl. Physiol. 68(3), J. S. Wyatta, et al., pp. 1086–1091.
"Spectrophotometric monitoring of arterial oxygen saturation in the fingertip", published in 1980 by Medical & Biologial Engineering & Computing, I. Yoshiya et al., 1980, pp. 27–32.
"Near-Infrared Sensing of Oxygenation", 5th Medical Photonics Meeting (MPM), Dr. D. T. Delpy, et al. pp. 17–20.
Biomedizinische Technik, vol. 35, 185–189 "Laserspektroskopische Erfassung der induzierten Hyperoxieeine tierexperimentella Studie beim Lamm" S. Schmidt.

*Primary Examiner*—Lee S. Cohen
*Assistant Examiner*—Robert L. Nasser, Jr.
*Attorney, Agent, or Firm*—Sughrue, Mion, Zinn, Macpeak & Seas

[57] ABSTRACT

A tissue oxygen measuring system enabling the automatic and continuous measurement of diagnosing items including cerebral blood flow, cerebral blood volume, and response of cerebral blood volume in arterial carbon dioxide tension uses an oxygen measuring system based on near infrared spectroscopy, a pulse oximeter, and an arterial carbon dioxide tension measuring unit. A gas blending unit is employed before a ventilator or face mask to control the ventilator so that a rate of a quantity of oxygen and/or a quantity of carbon dioxide to be blended in the air is changed at predetermined intervals. Trigger signals are produced in synchronism with the changes of the gaseous contents of the air, and parameters for computing information regarding the diagnosing items are measured in response to the trigger signals. With the repetitive measurements of the parameters, a signal-to-noise ratio can be improved by averaging the data and erroneous data can easily be identified.

17 Claims, 6 Drawing Sheets

TISSUE OXYGEN MEASURING SYSTEM

BACKGROUND OF THE INVENTION

The present invention relates to a tissue oxygen measuring system, and more particularly to such a system for automatically measuring at least one of cerebral blood flow, cerebral blood volume, and a response of cerebral blood volume to change in arterial carbon dioxide tension.

In general, in diagnosing the function of a body organ, such as the cerebral tissues, the fundamental and important parameters to measure are the oxygen quantity in the body organ and the organ's utilization of oxygen. Supplying body organs with a sufficient quantity of oxygen is indispensable for the growth ability of fetuses and new-born infants. If the supply of oxygen to a fetus is insufficient, the probability that the fetus will not survive or that the new-born infant will die is high. Even if the newborn infant lives, the serious problems may remain as a result of lack of a sufficient amount of oxygen. The insufficiency of oxygen affects every body organ, but especially causes serious damage in the cerebral tissues.

An oxygen quantity measuring system by near infrared ray (hereinafter referred to as "NIR oxygen measuring system") has been proposed in the art as disclosed, for example, in Japanese Laid-Open Patent Publication No. 63-275324. Briefly, in the NIR oxygen measuring system, near infrared rays (NIR) of selected wavelengths are directed through a flexible fiber optic bundle into one side of the head. Light emerging from the opposite side of the head is conveyed by an identical bundle to a photomultiplier tube operating in photon-counting mode. A computer calculates the changes in optical absorption at each wavelength and converts these into changes in oxy- and deoxyhemoglobin concentration ($\Delta[HbO_2]$ and $\Delta[Hb]$). Near infrared spectroscopy enables transillumination of the intact head and offers non-invasive quantization of cerebral blood volume.

It has also been proposed to quantify clinically important parameters by means of the NIR spectroscopy, which parameters including cerebral blood flow (CBF), cerebral blood volume (CBV), and a response of cerebral blood volume to change in arterial carbon dioxide tension (hereinafter referred to as "$CO_2$ response"). These parameters are clinically important for undergoing therapy for particularly newborn infants who have various cerebral lesions. Actual measurements of CBF, CBV and $CO_2$ response have proven the clinical importance of these parameters. The ranges of measured values in each parameter are notably different between newborn infants with normal brains and infants with brain injury born, as reported in the publications cited below.

Measurements of CBF, CBV, and $CO_2$ response will be described.

(1) Measurement of CBF

A method of measuring CBF by means of NIR spectroscopy is described in the publication entitled "THE LANCET", Oct. 1, 1988, pp. 770–771.

In measuring CBF, the change of oxyhemoglobin ($\Delta HbO_2$) is used as a tracer. Representing the cerebral oxyhemoglobin concentration per a unit volume (1 ml) of a cerebral tissue as Q ($\mu$mol/ml); the change of oxygen saturation in the arterial blood and the venous blood as $\Delta SaO_2$ (%) and $\Delta SvO_2$ (%), respectively; and flow of blood in the organ as F ($\mu$mol/ml.min) as F, the following equation is established according to the Fick principle:

$$\frac{dQ}{dt} = F(\Delta SaO_2 - \Delta SvO_2) \quad (\mu \cdot mol/ml \cdot min) \quad (1)$$

The Fick principle states that the rate of accumulation (dQ/dt) of the tracer substance, $\Delta HbO_2$, in an organ is equal to the difference between the rate of arrival and the rate of departure of that substance. It is to be noted that in equation (1), changes in cerebral oxyhemoglobin (dQ/dt) can be measured at every 1 to 2 seconds by the NIR oxygen measuring system.

If a substance is suddenly introduced into the arterial blood, a measurement of the amount accumulated in the organ can be made at a specific time (t) later. When t is less than 10 seconds, the tracer generally does not appear in the venous blood. Stated differently, 10 seconds is a time during which the change of the tracer does not appear in the venous blood, i.e., $\Delta SvO_2 = 0$.

The arterial oxygen saturation can be measured by a pulse oximeter. Since the venous oxygen saturation cannot be measured by the pulse oximeter, the measurement is performed within the period when the changes of the tracer is not observed in the venous blood. Integrating both sides of equation (1) under the condition of $\Delta SvO_2$, the following equation is obtained:

$$Q = F \cdot \int_0^t \Delta SaO_2 dt \quad (2)$$

$$F = Q \cdot \frac{1}{\int_0^t \Delta SaO_2 dt} \quad (\mu mol/ml \cdot min) \quad (3)$$

Each of the items in right side of equation (3) is known, so that CBF can be measured. Measurement of CBF is performed in such a manner that following a period when $HbO_2$ and $SaO_2$ are stable, a sudden transient increment of 5 to 10% in $SaO_2$ is induced by increasing the inspired oxygen concentration for a few breaths. During the measurement, blood pressure and values for transcutaneous carbon dioxide tension ($PaCO_2$) are within normal range.

(2) Measurement of Cerebral Blood Volume (CBV)

A method of measuring CBV is disclosed in the publication entitled "J. Appl. Physiol.68(3)", pp. 1086–1091.

CBV can be defined by the sum of oxy- and deoxyhemoglobin concentration. Therefore, the following equation is established.

$$CBV = Hb + HbO_2 \quad (4)$$

As mentioned above, the arterial saturation ($SaO_2$) can be given from the results of the measurements by means of the pulse oximeter.

$$SaO_2 = \frac{HbO_2}{HbO_2 + Hb} \quad (5)$$

Because it is assumed that CBV does not change during the maneuver, the changes in $[HbO_2]$ and $[Hb]$ must be equal and opposite. Hence, from the above two equations, the following equation results.

$$CBV = \frac{\Delta HbO_2}{\Delta SaO_2} = \frac{-\Delta Hb}{\Delta SaO_2} = \frac{\Delta(HbO_2 - Hb)}{2\Delta SaO_2} \quad (6)$$

(3) Measurement of CO₂ Response

The measurement of the $CO_2$ response is performed while cyclically changing carbon dioxide levels caused either by the addition of a small percentage of $CO_2$ to the patient's gases or by a small cyclic variation in the rate of ventilation. The cycles are at a lower frequency, one every 2 to 10 minutes, since the technique relies on an equilibrium being maintained between the saturations in all blood vessels in the organ.

As described above, the measurement of CBF relies on inducing a rapid change in the patient's arterial hemoglobin saturation and then the rate of increase in oxyhemoglobin concentration is observed via the NIR oxygen measuring system. The change in arterial saturation is made by manually and rapidly altering the concentration of oxygen the patient is breathing. Specifically, the quantity of oxygen supplied to the patient from a ventilator is generally changed during 2 to 3 seconds. On the other hand, to measure CBV, the quantity of oxygen is smoothly changed over several minutes. To measure the response of CBV, the amount of carbon dioxide to be blended in the air is also smoothly changed over several minutes. Those procedures have also been done manually and the measurements of those three parameters have been performed individually.

For the reasons stated above, it has not been possible to continuously measure each of the three parameters notwithstanding the fact that data derived from continuous measurements are needed to improve accuracy and to identify erroneous data. Further, the individual measurements of the three parameters are intricate for the clinician.

SUMMARY OF THE INVENTION

The present invention has been made to solve the aforesaid conventional drawbacks, and accordingly it is an object of the present invention to provide a tissue oxygen measuring system which enables repetitive measurements of at least one of three parameters.

To achieve the above and other objects, there is provided a tissue oxygen measuring system which comprises a ventilator unit for supplying air to a living subject for the living subject to breath; a control unit connected to the ventilator unit for controlling the ventilator unit to cyclically change the gaseous content of the air at a predetermined interval; means for producing trigger signals in timed relation to the cyclic changes of the gaseous content of the air; measuring means for measuring oxygen in the tissue of the living subject and supplying data regarding measured results; and a data processing unit responsive to the trigger signals for receiving the data from the measuring means and based on it cyclically computing information regarding blood flowing in the tissue. The control unit controls the ventilator unit to cyclically change a rate of at least one of oxygen quantity and carbon dioxide quantity to be contained in the air.

The measuring means comprises a first measuring unit for measuring changes in oxyhemoglobin and dioxyhemoglobin in blood flowing in the tissue by near infrared ray spectroscopy, and a second measuring unit for measuring a saturation of oxygen in an artery. The data processing unit cyclically computes either a cerebral blood flow or a cerebral blood volume or both based on the data received from the first and second measuring units.

The tissue oxygen measuring system may further comprises second measuring means for measuring an arterial carbon dioxide tension of the living subject and providing data regarding measured results, wherein the data processing unit cyclically computes a ratio of change in cerebral blood volume to change in arterial carbon dioxide tension based on the data provided by the second measuring means. The data processing unit may further cyclically compute the cerebral blood flow or the cerebral blood volume or both together with the ratio of change in cerebral blood volume to change in arterial carbon dioxide tension.

To improve a signal-to-noise ratio, averaging means may be provided to provide average data for a plurality of data regarding each of the cerebral blood flow, cerebral blood volume, and the ratio of change in cerebral blood volume to change in arterial carbon dioxide tension obtained through the cyclic changes of the gaseous contents of the air.

Display means may be provided for displaying results computed by the data processing unit and/or the average data given by the averaging means.

The above and other objects, features and advantages of the present invention will become more apparent from the following description when taken in conjunction with the accompanying drawings in which preferred embodiments of the present invention are shown by way of illustrative examples.

DETAILED DESCRIPTION OF THE PREFERRED EMBODIMENTS

Figure 1:
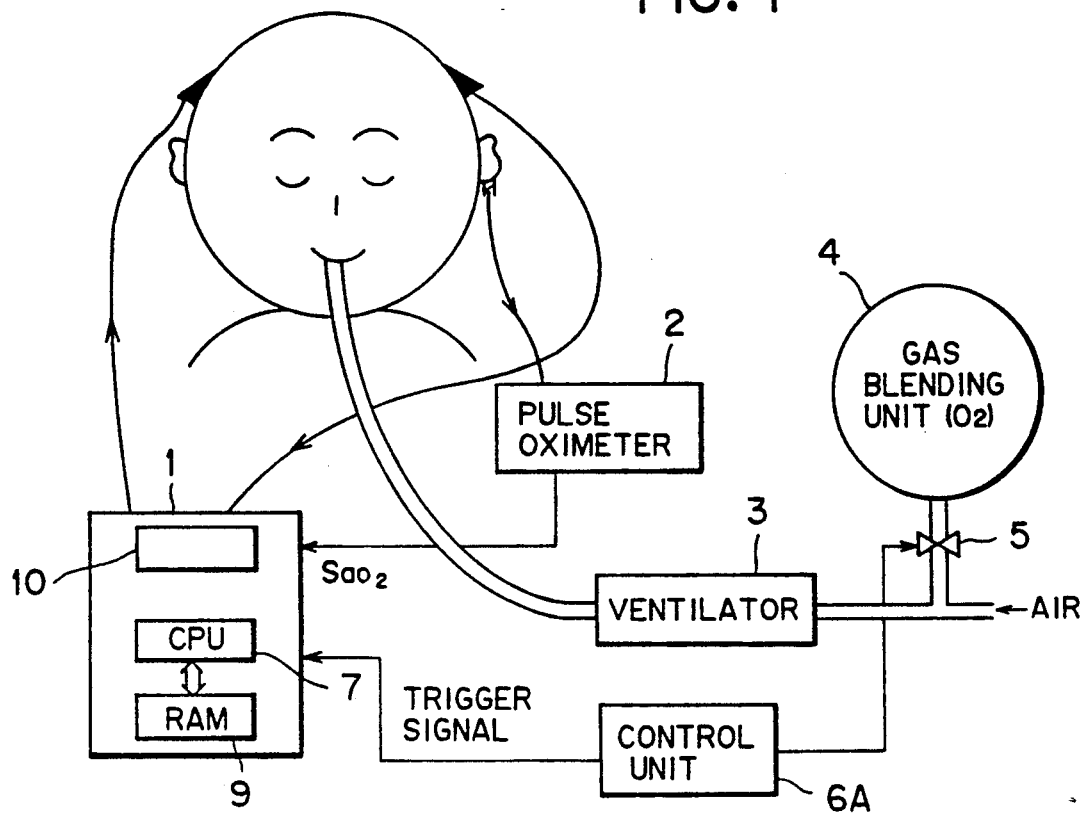
FIG. 1 is a schematic diagram illustrating an arrangement of the tissue oxygen measuring system according to the present invention.

Referring to FIG. 1, shown is an arrangement of the tissue oxygen measuring system for measuring each of CBF and CBV. The timing charts for the measurements of CBF and CBV and their data processing sequences are illustrated in FIGS. 4A and 4B, respectively.

The system is basically comprised of an NIR oxygen measuring apparatus 1 for measuring quantity of oxygen, a pulse oximeter 2 for measuring arterial saturation ($SaO_2$), a ventilator 3 for supplying air to the patient, a gas blending unit 4 disposed downstream of the ventilator 3 and connected thereto via a valve 5, and a control unit 6A connected between the NIR oxygen measuring apparatus 1 and the gas blending unit 4 for controlling the valve 5, thereby controlling a quantity of oxygen to be introduced into the ventilator 3. The gas blending unit 4 produces a gas mixture which on average has the correct oxygen concentration for the patient, but which has imposed upon it a regular square wave oscillation of a low frequency by means of the control unit 6A. This oscillation does not have a harmful effect on the patient, as a similar modulation is used in respiratory physiology laboratories for lung function studies.

Figure 4A:
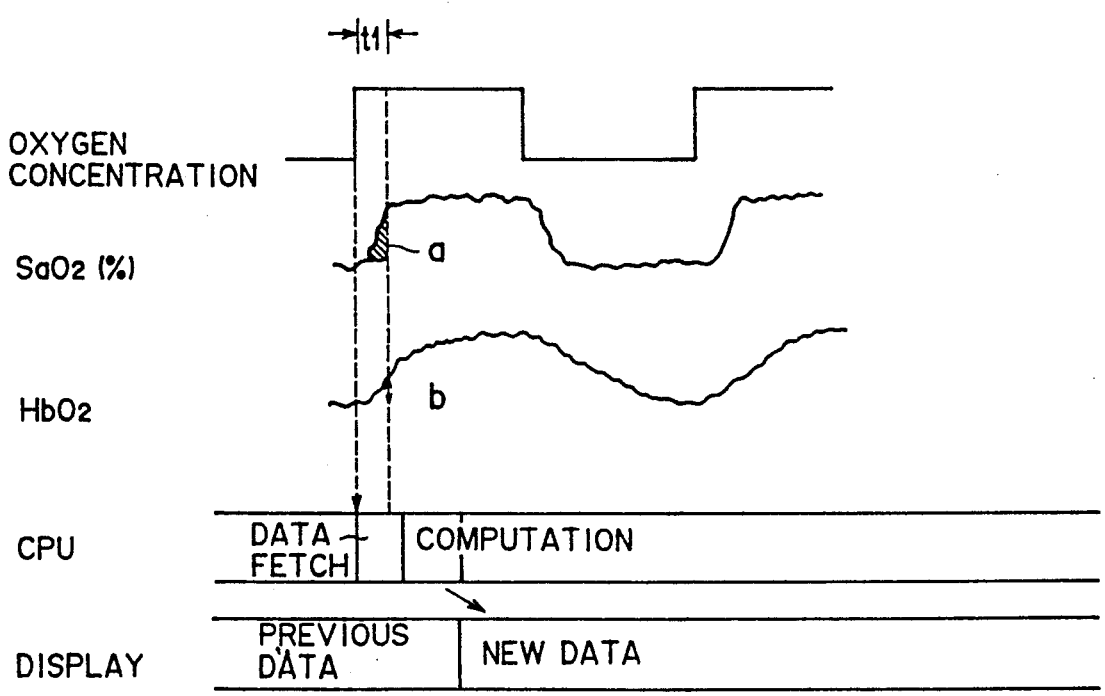
FIGS. 4A through 4E are timing charts for measuring each of CBF, CBV, and $CO_2$ response and a combination thereof.
Figure 4B:
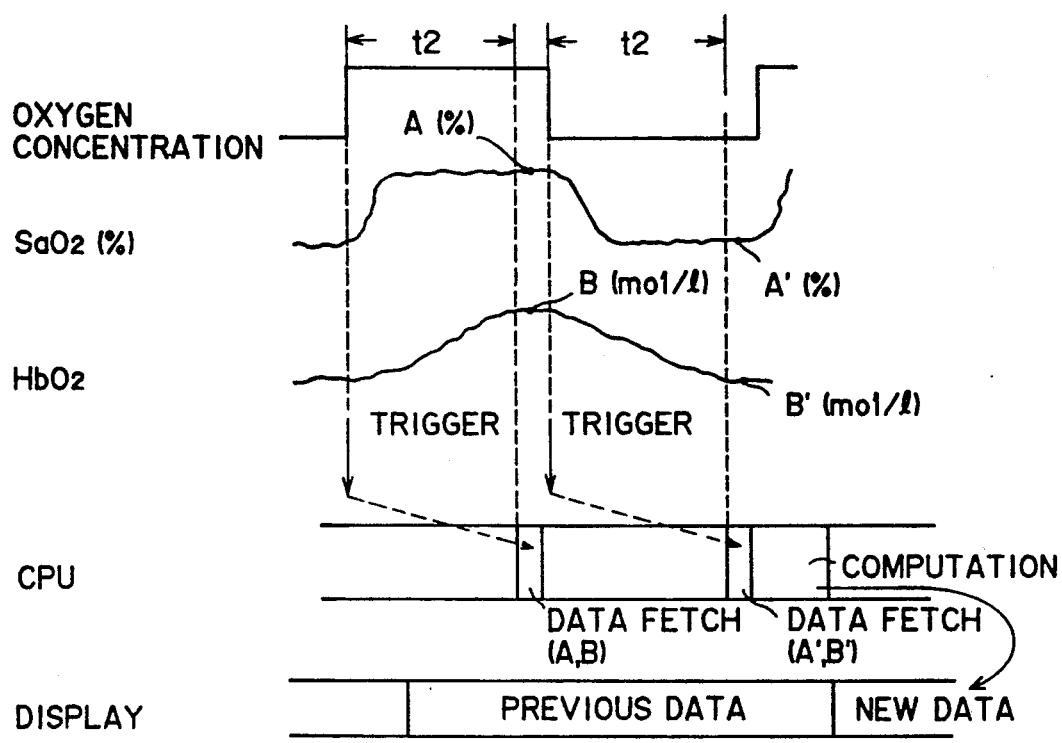

The control unit 6A controls the valve 5 of the gas blending unit 4 at a given frequency, so that the rate of oxygen quantity to a unit volume of air is periodically changed as shown in FIGS. 4A and 4B. More specifically, with the control unit 6A, the oxygen concentration is increased and maintained at a high level for a predetermined period of time ranging from 1 to 10 seconds and is then decreased to a normal level for an equal predetermined period of time. The arterial saturation ($SaO_2$) and the change in the quantity of oxyhemoglobin ($\Delta HbO_2$) in the patient's brain are repeatedly and continuously measured by the pulse oximeter 2 and the NIR oxygen measuring apparatus 1, respectively, during a transit period of time $t_1$ ranging from 1 to 10 seconds at which the concentration of oxygen is abruptly changed.

The NIR oxygen measuring apparatus 1 incorporates a central processing unit (CPU) 7 therein which is supplied with trigger signals from the control unit 6A. The trigger signals are issued from the control unit 6 in synchronism with the control of the valve 5. In response to the trigger signal, the CPU 7 fetches data from both the NIR oxygen measuring apparatus 1 and the pulse oximeter 2. Data regarding the change in oxyhemoglobin concentration [$HbO_2$] is supplied from the NIR oxygen measuring apparatus 1, which data is represented by Q in equation (3) and is obtained as a difference b (see FIG. 4A) in the level of the oxyhemoglobin concentrations at the start and end of time $t_1$. Further, data regarding the arterial oxygen saturation ($SaO_2$) during time $t_1$ is supplied from the pulse oximeter 2, which data corresponds to an area indicated by oblique lines in FIG. 4A and denoted by letter a. Those data supplied from both the NIR oxygen measuring apparatus 1 and the pulse oximeter 2 are temporarily stored in random access memory (RAM) 9 connected via a bus to the CPU 7. Based on those data, the CPU 7 performs arithmetic operations in accordance with equation (3) upon reading the data out of the RAM 9. The results of the computation by the CPU 7 is digitally displayed on a display 10 of the apparatus 1. In this manner, a plurality of CBF data are obtained through the repetitive measurements and computations and are collectively displayed on the display 10.

Computation of CBV is performed in accordance with the sequence indicated in FIG. 4B. Specifically, after expiration of time $t_2$ from the occurrence of the trigger signal in the oxygen-increased cycle, the CPU 7 fetches data A regarding the arterial saturation ($SaO_2$) from the pulse oximeter 2 and data B regarding the concentration of oxyhemoglobin from the NIR oxygen measuring apparatus 1, and temporarily stores those data in the RAM 9. Then, after expiration of time $t_2$ from the subsequent trigger signal occurring at the start of the next oxygen-reduced cycle, the same kinds of data A' and B' are fetched and stored in different storage locations of the RAM 9. Then, using the data stored in the RAM 9, the CPU 7 performs arithmetic operation in accordance with the equation of $CBV=(\Delta HbO_2)/(\Delta SaO_2)$ mentioned previously. That is, CBV is obtained through the computation of $(B-B')/(A-A')$. Upon completion of the computation, the CPU 7 displays the resultant data in the display 10.

Figure 2:
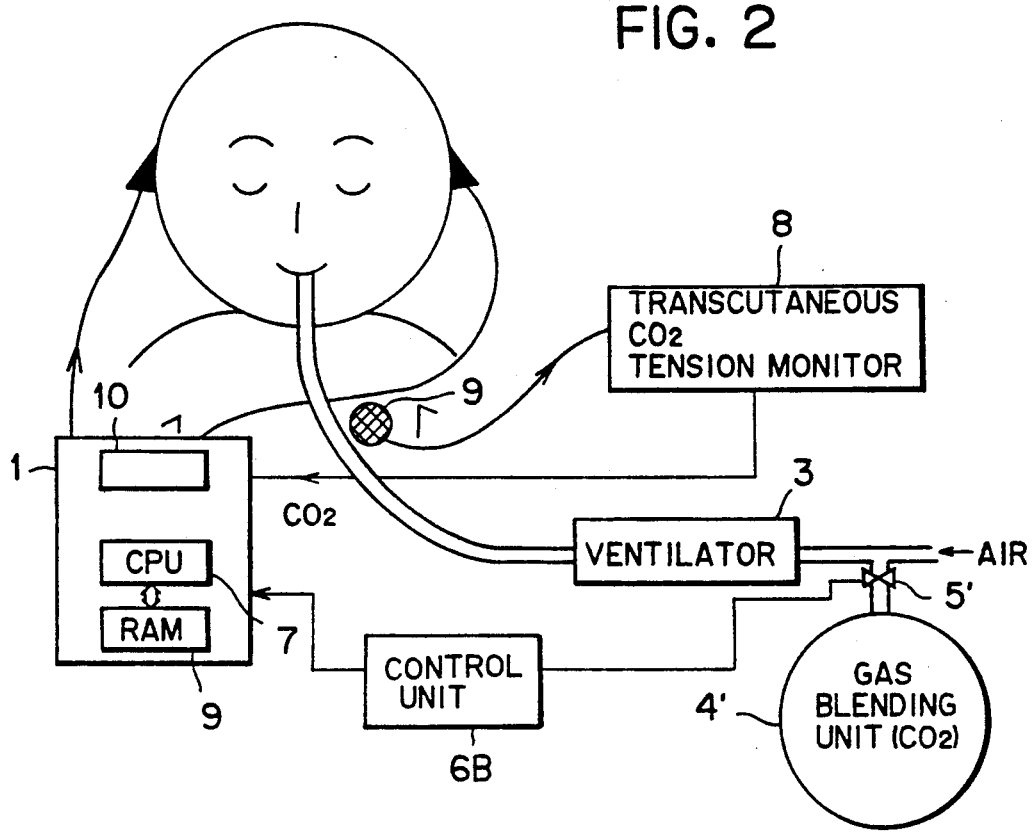
FIG. 2 is a schematic diagram illustrating another arrangement of the tissue oxygen measuring system according to the present invention.

A similar sequence can be employed for the automated measurement of the $CO_2$, with the use of a small but cyclic change in carbon dioxide levels. The arrangement shown in FIG. 2 is used for such a measurement, which includes the NIR oxygen measuring apparatus 1, a transcutaneous carbon dioxide ($CO_2$) tension monitor 8, a gas blending unit 4', and a control unit 6B for controlling a valve 5' of the gas blending unit 4'. The monitor 8 has a sensor 11 for attachment to the patient's skin to measure arterial carbon dioxide tension ($PaCo_2$) which tension will hereinafter referred to as "$CO_2$ tension". The control unit 6B in the arrangement of FIG. 2 controls the valve 5' of a gas blending unit 4' which in this case introduces carbon dioxide into the ventilator 3.

Figure 4C:
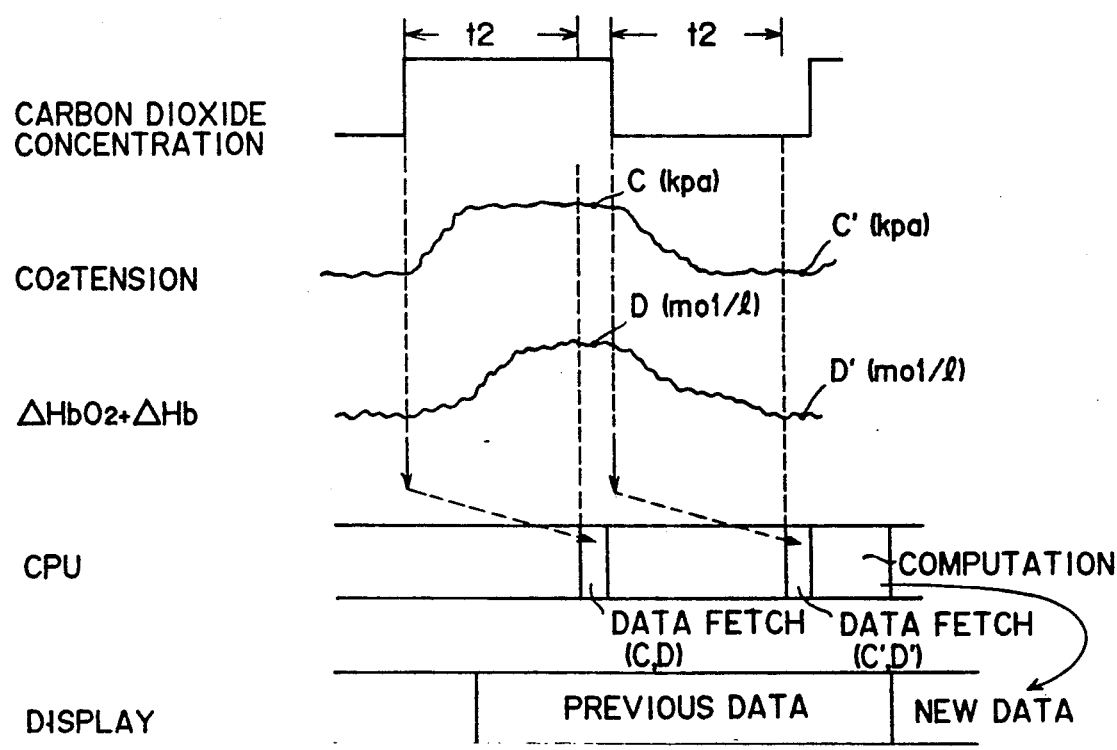

The sequence for measurement of the $CO_2$ response is illustrated in FIG. 4C. After expiration of time $t_2$ from the occurrence of the trigger signal at the start of the carbon-dioxide-increase cycle, the CPU 7 fetches data C regarding the $CO_2$ tension from the monitor 8, and data D regarding a total quantity of the changes in oxy- and dioxyhemoglobin ($\Delta HbO_2 + \Delta Hb$) from the NIR oxygen measuring apparatus 1. Those data are temporarily stored in the RAM 9. In the subsequent carbon-dioxide-reduced cycle, the same kinds of data C' and D' are similarly fetched and stored. Then, the CPU 7 performs arithmetic operation to provide a ratio of the change in ($\Delta HbO_2 + \Delta Hb$) to a change of the arterial carbon dioxide tensions attendant to the change of the quantity of $CO_2$. That is, the CPU 7 performs computation of $(D-D')/(C-C')$. By repeatedly carrying out the above measurements and computations, a plurality of the $CO_2$ response data are obtained successively.

Figure 4D:
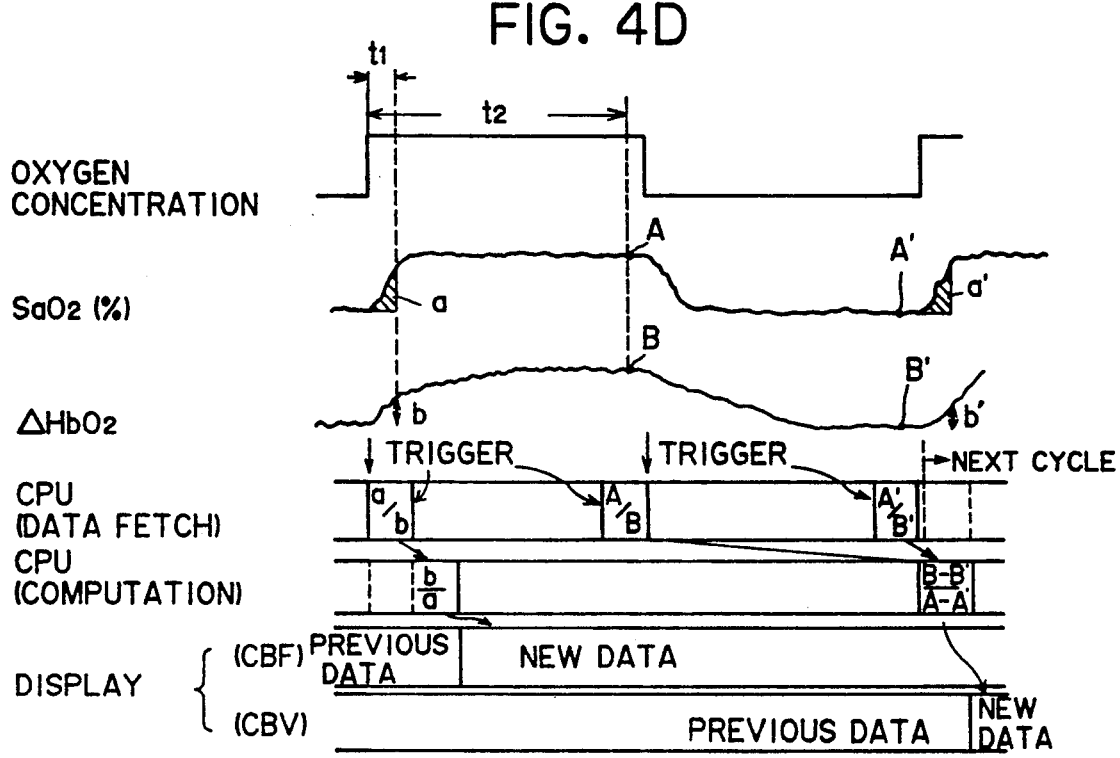

As shown in FIG. 4D, both the CBF and CBV can be continuously measured with the arrangement shown in FIG. 1 in accordance with the combined sequence for CBF and CBV.

The control unit 6A periodically changes the oxygen concentration contained in the air supplied to the patient as described previously. During a transit time $t_1$ in the oxygen-increased cycle, data regarding $SaO_2$ and $\Delta HbO_2$ measured, respectively, by the pulse oximeter 2 and the NIR oxygen measuring apparatus 1 are fetched and stored in the RAM 9, whereupon CBF is computed and displayed.

After expiration of time $t_2$ from the occurrence of the trigger signal in the same oxygen-increased cycle, data A regarding the arterial saturation ($SaO_2$) and data B regarding the concentration of oxyhemoglobin measured, respectively, by the pulse oximeter 1 and the NIR oxygen measuring apparatus 1 are fetched and stored in the relevant storage locations of the RAM 9. Then, after expiration of time $t_2$ from the subsequent trigger signal occurring at the start of the next oxygen-reduced cycle, the same kinds of data A' and B' are fetched and stored in the RAM 9. Then, the CPU 7 computes CBV and displays it together with the CBF.

Figure 3:
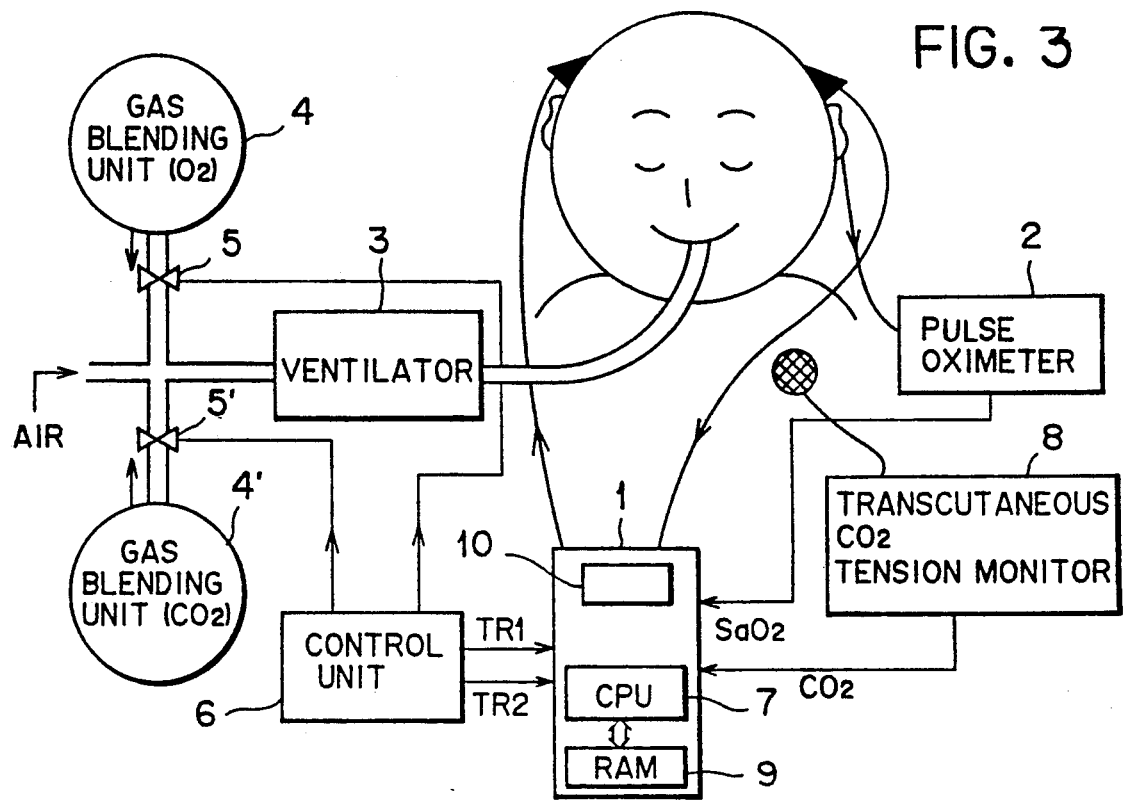
FIG. 3 is a schematic diagram illustrating still another arrangement of the tissue oxygen measuring system according to the present invention.
Figure 4E:
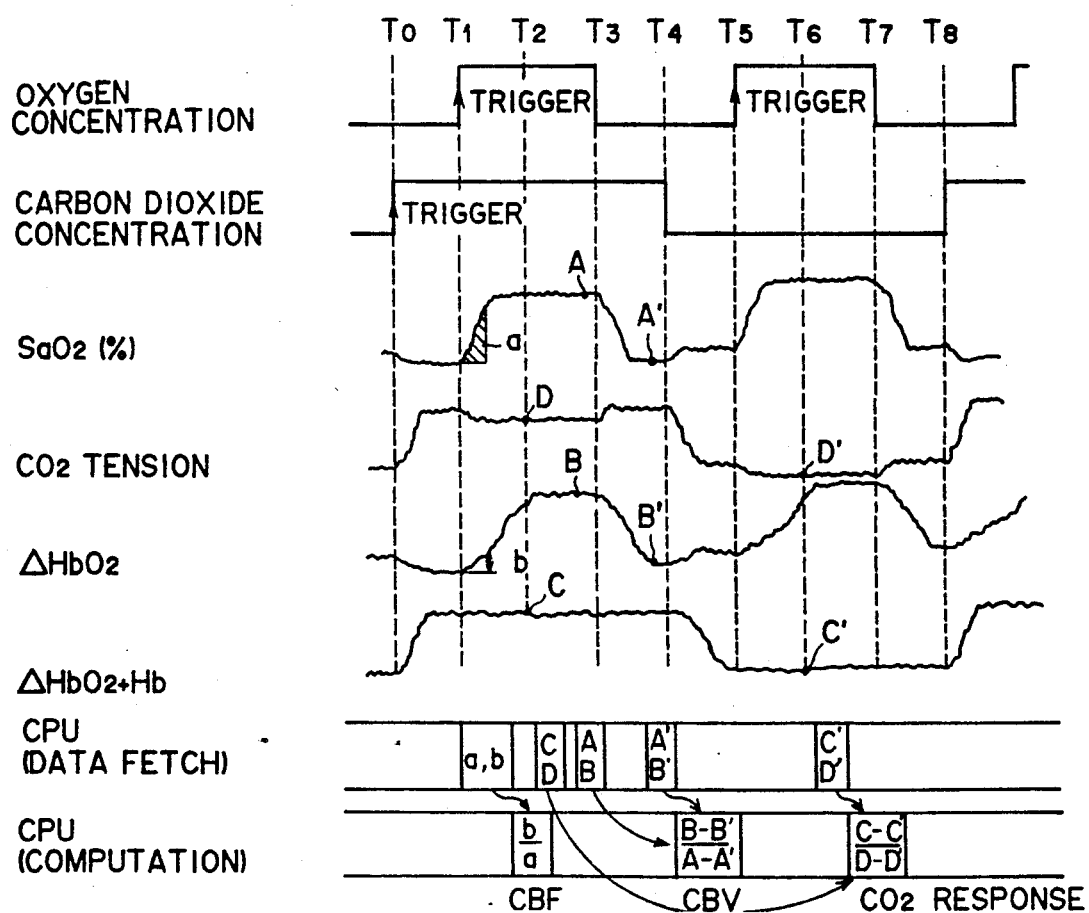

FIG. 3 shows an arrangement for automated measurement of CBF, CBV and $CO_2$ response. The arrangement of FIG. 3 includes the NIR oxygen measuring apparatus 1, the pulse oximeter 2, the ventilator 3, the control unit 6, and the transcutaneous carbon dioxide tension monitor 8. In this embodiment, both the oxygen blending unit 4 and the carbon dioxide blending unit 4' are connected to the ventilator 3 through the valves 5 and 5', respectively. The control unit 6 controls the valves 5 and 5' so that opening and closing thereof are performed at different timings from each other and the frequency for the valve 5 to perform the opening and closing actions is two times larger than that for the valve 5' to perform the same actions. The oxygen-increased duration takes place in the midst of the $CO_2$-increased or $CO_2$-reduced duration. More specifically, in FIG. 4E, the valve 5' is opened at time $T_0$, the valve 5 is opened at time $T_1$ and closed at time $T_3$, and the valve 5' is closed at time $T_4$. The valve 5 is again opened at time $T_5$ and closed at time $T_7$ and the valve 5' again opened at time $T_8$. Note that an interval between $T_{i+1}$ and $T_i$ is time t where i is an integer.

Figure 5A:
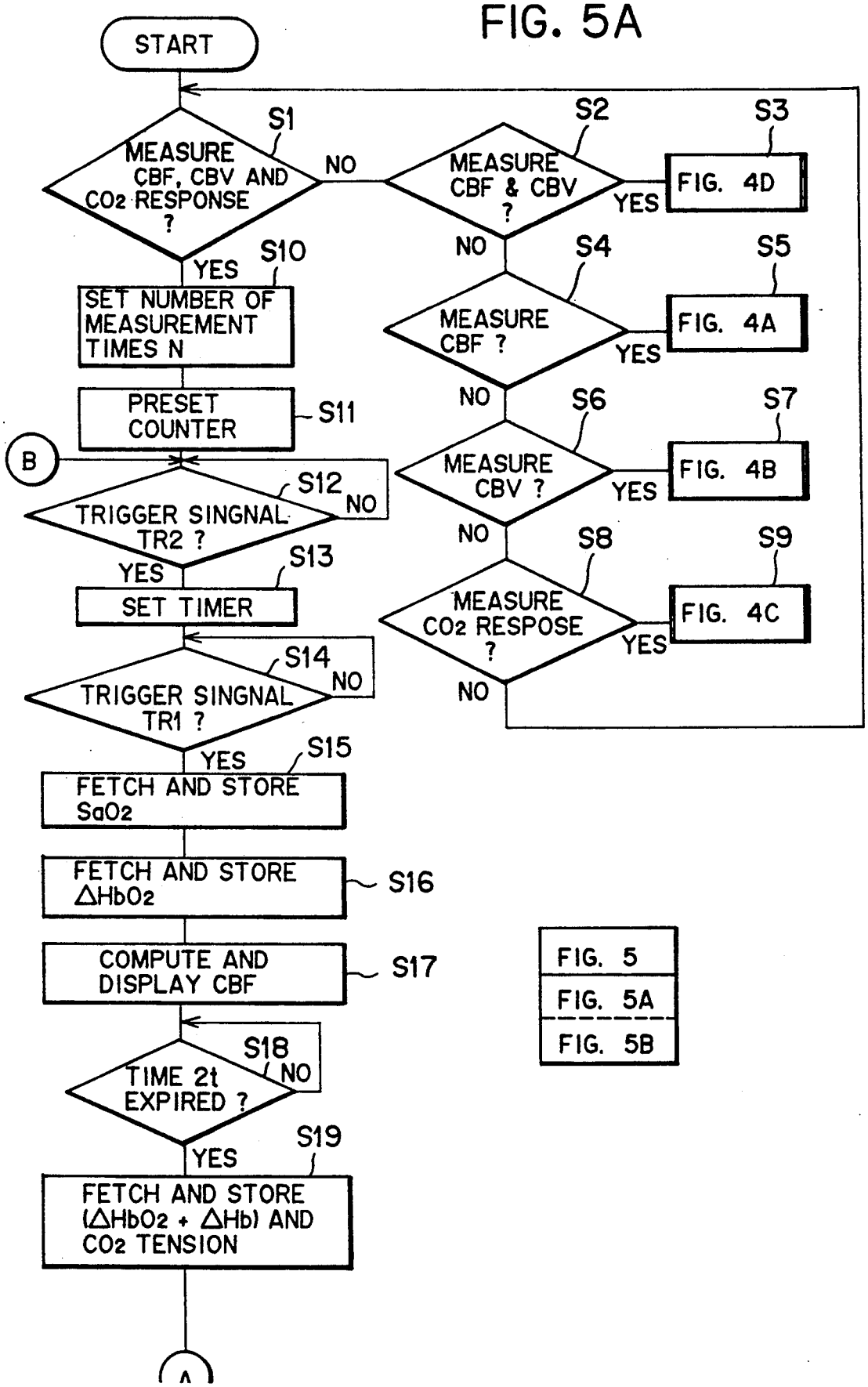
FIG. 5a and 5b are flow charts for description of the sequence for measuring CBF, CBV and $CO_2$ response.
Figure 5B:
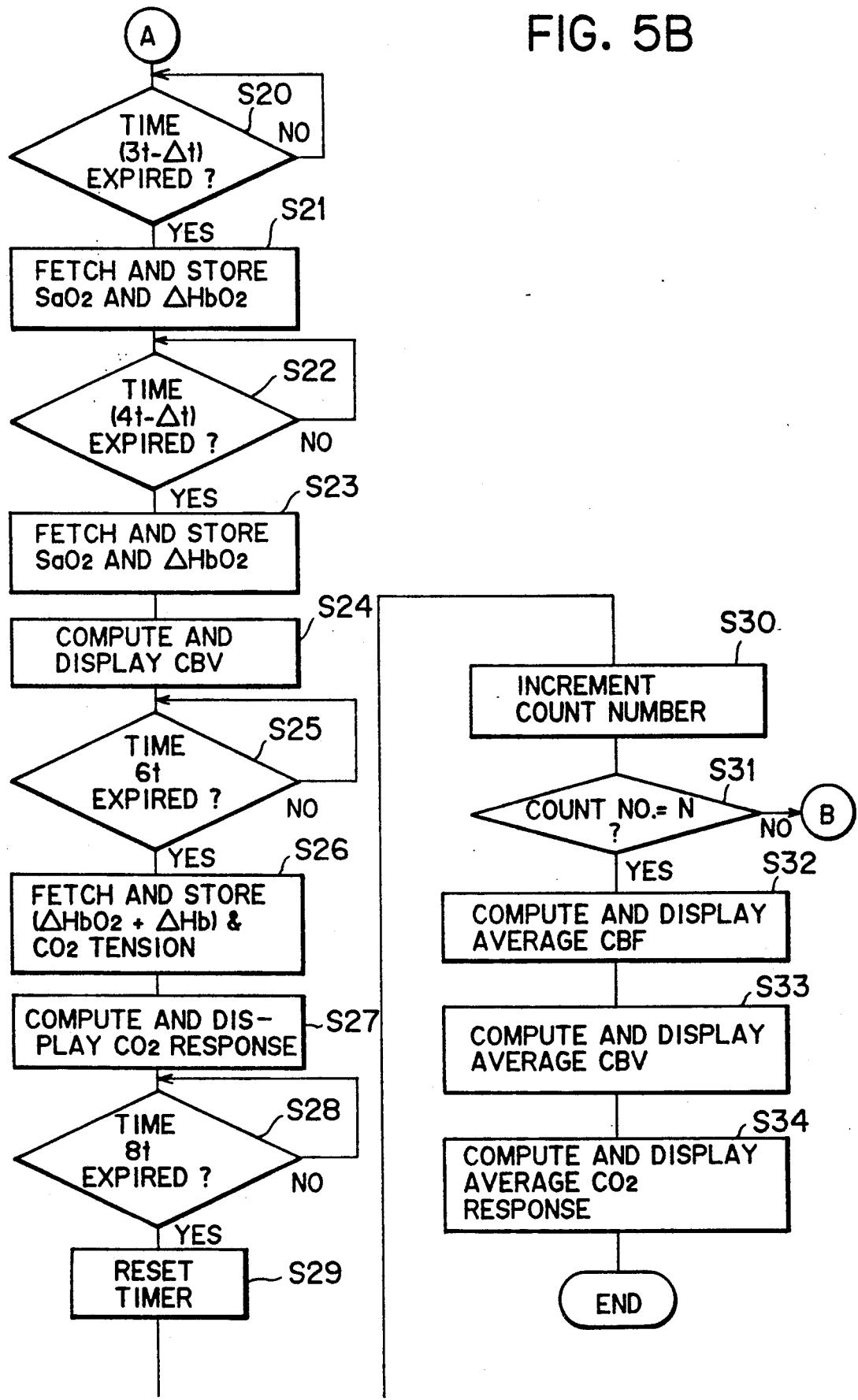

The automated measurements of CBF, CBV and $CO_2$ response are implemented by the combined sequence described with reference to FIGS. 4A, 4B and 4C. The sequence will be described while referring to the flow chart shown in FIG. 5.

Upon start of the measurement, the operator inputs the measuring items through a keyboard (not shown) connected to the CPU 7. When the items of CBF, CBV and $CO_2$ response are selected, the routine proceeds to step S10. If the items of CBF and CBV are selected in step S2, the processing described with reference to FIG. 4D is executed in step S3. If the item of CBF is selected in step S4, the processing described with reference to FIG. 4A is executed in step S5. If the item of CBV is selected in step S6, the processing described with reference to FIG. 4B is executed in step S7. If the item of $CO_2$ response is selected in step S8, the processing described with reference to FIG. 4C is executed in step S9.

In step S10, the number of measurement times N of the three items is set, and a counter provided interiorly of the CPU 7 is cleared in step S11. Next, it is determined in step S12 whether the trigger signal TR2 is detected. The trigger signal TR2 is issued from the control unit 6 in synchronism with the opening of the valve 5' of the carbon dioxide blending unit 4' allowing to blend a small predetermined quantity of $CO_2$ into the air. The trigger signals TR2 are issued whenever the valve 5' is opened, and the valve 5' is closed by the control of the control unit 6 after expiration of 4t from the receipt of the trigger signal TR2. When the trigger signal is detected in step S12, a timer provided interiorly of the CPU 7 is set to start measuring time in step S13. In step S14, it is further determined whether the trigger signal TR1 is detected. The trigger signal TR1 is also issued from the control unit 6 in synchronism with the opening of the valve 5 of the oxygen blending unit 4 allowing to blend a predetermined quantity of oxygen into the air. The trigger signals TR1 are issued whenever the valve 5 is opened, and the valve 5 is closed by the control of the control unit 6 after expiration of 2t from the receipt of the trigger signal TR1.

If both the trigger signals TR2 and TR1 are detected, data regarding $SaO_2$ is fetched from the pulse oximeter 2 and stored in the RAM 9 in step S15. Thereafter, data regarding $\Delta HbO_2$ is fetched from the NIR oxygen measuring apparatus 1 and stored in the relevant storage location of the RAM 9 in step S16. Then, the CPU 7 computes CBF based on the data regarding $SaO_2$ and $\Delta HbO_2$ and displays the resultant data in the display 10 in step S17.

Next, in step S18 it is determined whether time 2t has been expired or not while referring to the timer. If yes, data regarding $(\Delta HbO_2 + \Delta Hb)$ and the $CO_2$ tension are fetched from the NIR oxygen measuring apparatus 1 and the carbon tension monitor 8, respectively, and are stored in the relevant storage locations of the RAM 9 in step S19.

In step S20, it is determined whether time $(3t - \Delta t)$ has been expired while referring to the timer. If yes, data regarding $SaO_2$ and $\Delta HbO_2$ are fetched respectively from the pulse oximeter 2 and the NIR oxygen measuring apparatus 1 and stored in the RAM 9 in step S21. That is, immediately before the valve 5 of the oxygen blending unit 4 is closed, those data are fetched therefrom. This is because the cerebral tissue is in a stable condition with the supply of air containing oxygen and carbon dioxide at a predetermined ratio. In step S22, it is determined whether time $(4t - \Delta t)$ has been expired while referring to the timer. If the determination made in step S22 is yes, then data regarding $SaO_2$ and $\Delta HbO_2$ are again fetched and stored in step S23. That is, immediately before the valve 5' of the carbon dioxide blending unit 4' is closed, those data are fetched. Based on data stored in steps S21 and S24, CBV is computed and the resultant data is displayed in step S24.

In step S25, it is determined whether time 6t has been expired while referring to the timer. If yes, $(\Delta HbO_2 + \Delta Hb)$ and $CO_2$ tension are fetched respectively from the NIR oxygen measuring apparatus 1 and the $CO_2$ tension monitor 8 and are stored in the RAM 9 in step S26. In step S27, the CPU 7 performs arithmetic operation based on the data fetched in steps S19 and S26 and provides data regarding $CO_2$ response for displaying the latter in the display 10.

Through the steps S12 through S27, measurements of the three items in one cycle have been completed. In step S28, it is determined whether time 8t has been expired, and if yes, the timer is reset in step S29, and the count number of the internal counter is incremented by one in step S30. Next, it is determined in step S31 whether the count number is equal to N. If no, the routine returns to step S12, and the measurement in the next cycle is performed, whereas if yes, the CPU 7 executes arithmetic operations to provide average data regarding each of CBF, CBV and $CO_2$ response based on the results of measurements through N cycles and displays the resultant data in the display in steps S32 through S34, whereupon the routine ends.

The above-described sequence according to the present invention can be implemented in the operating theater or intensive care unit (ICU), linked to the ventilator. Since the signal is repetitive, it is possible to employ signal averaging techniques to improve a signal-to-noise (S/N) ratio and to identify erroneous data. Similarly, because one would be averaging, it should be possible to employ smaller swings in the saturation and still obtain accurate results. A further advantage of the repetitive nature of the readings is that one could obtain information on the time delay between the change detected by the pulse oximeter or the $CO_2$ monitor and that observed by the NIR oxygen measuring apparatus.

While the present invention has been described with reference to specific embodiments, the addition of a small percentage of $CO_2$ or the addition of oxygen may be made to be in sinusoidal waveform to smoothly change the contents of air to be supplied to the patient. Further, the ventilator can be triggered by the NIR oxygen measuring apparatus or vice versa.

I claim:
1. A tissue oxygen measuring system comprising:
   a ventilator unit for supplying air to a living subject for the living subject to breath;

a control means connected to said ventilator unit for controlling said ventilator unit to cyclically change gaseous content of the air at a predetermined interval;

means for producing trigger signals in timed relation to the cyclic changes of the gaseous content of the air;

measuring means for measuring oxygen in a tissue of the living subject and supplying data regarding measured results; and a data processing means responsive to the trigger signals for receiving the data from said measuring means and based on said trigger signals cyclically computing information regarding blood flowing in the tissue.

2. A tissue oxygen measuring system according to claim 1, wherein said measuring means comprises a first measuring means for measuring changes in oxyhemoglobin and dioxyhemoglobin in blood flowing in the tissue by near infrared ray spectroscopy, and a second measuring means for measuring a saturation of oxygen in an artery.

3. A tissue oxygen measuring system according to claim 2, wherein said data processing means includes means for cyclically computing at least one of a cerebral blood flow and a cerebral blood volume based on the data received from said first and second measuring units.

4. A tissue oxygen measuring system according to claim 3, further comprising third measuring means for measuring an arterial carbon dioxide tension of the living subject and providing data regarding measured results.

5. A tissue oxygen measuring system according to claim 4 wherein said data processing means cyclically computes a ratio of change in cerebral blood volume to change in arterial carbon dioxide tension.

6. A tissue oxygen measuring system according to claim 5, wherein said data processing means cyclically computes the cerebral blood flow, the cerebral blood volume, and the ratio of change in cerebral blood volume to change in arterial carbon dioxide tension.

7. A tissue oxygen measuring system according to claim 3, wherein said control means includes means for controlling said ventilator unit to cyclically change a rate of one of oxygen quantity and carbon dioxide quantity to be contained in the air.

8. A tissue oxygen measuring system according to claim 3, further comprising display means for displaying results computed by said data processing means.

9. A tissue oxygen measuring system according to claim 3, further comprising averaging means for averaging a plurality of data regarding each of the cerebral blood flow, the cerebral blood volume, and the ratio of change in cerebral blood volume to change in arterial carbon dioxide tension obtained through the cyclic changes of the gaseous contents of the air.

10. A tissue oxygen measuring system according to claim 2, further comprising third measuring means for measuring an arterial carbon dioxide tension of the living subject and providing data regarding measured results.

11. A tissue oxygen measuring system according to claim 10, wherein said data processing means cyclically computes a ratio of change in cerebral blood volume to change in arterial carbon dioxide tension.

12. A tissue oxygen measuring system according to claim 11 wherein said data processing means cyclically computes the cerebral blood flow, the cerebral blood volume, and the ratio of change in cerebral blood volume to change in arterial carbon dioxide tension.

13. A tissue oxygen measuring system according to claim 10 wherein said control means controls said ventilator unit to cyclically change a rate of carbon dioxide quantity to be contained in the air to cause the arterial carbon dioxide tension of the living subject to change.

14. A tissue oxygen measuring system according to claim 10 wherein said third measuring means comprises means for cyclically changing a rate of ventilation to cause the arterial carbon dioxide tension of the living subject to change.

15. A tissue oxygen measuring system according to claim 2, wherein said control means includes means for controlling said ventilator unit to cyclically change a rate of one of oxygen quantity and carbon dioxide quantity to be contained in the air.

16. A tissue oxygen measuring system according to claim 2 further comprising display means for displaying results computed by said data processing means.

17. A tissue oxygen measuring system according to claim 2 further comprising averaging means for averaging a plurality of data regarding each of the cerebral blood flow, the cerebral blood volume, and the ratio of change in cerebral blood volume to change in arterial carbon dioxide tension obtained through the cyclic changes of the gaseous contents of the air.

* * * * *